United States Patent
Lee

(10) Patent No.: US 11,774,432 B2
(45) Date of Patent: Oct. 3, 2023

(54) BIOCAPACITIVE BOD SENSOR

(71) Applicant: OZ Optics Ltd., Ottawa (CA)

(72) Inventor: Hyung-Sool Lee, Waterloo (CA)

(73) Assignee: OZ Optics Ltd., Ottawa (CA)

( * ) Notice: Subject to any disclaimer, the term of this patent is extended or adjusted under 35 U.S.C. 154(b) by 745 days.

(21) Appl. No.: 16/526,232

(22) Filed: Jul. 30, 2019

(65) Prior Publication Data

US 2020/0041476 A1    Feb. 6, 2020

(30) Foreign Application Priority Data

Jul. 31, 2018  (CA) ................................ CA 3012940

(51) Int. Cl.
| | |
|---|---|
| *C02F 3/28* | (2023.01) |
| *H01M 8/16* | (2006.01) |
| *H01M 8/24* | (2016.01) |
| *G01N 27/22* | (2006.01) |
| *G01N 27/327* | (2006.01) |
| *G01N 33/18* | (2006.01) |
| *G01N 27/409* | (2006.01) |

(52) U.S. Cl.
CPC ......... *G01N 33/1806* (2013.01); *G01N 27/22* (2013.01); *G01N 27/3273* (2013.01); *G01N 27/409* (2013.01); *G01N 33/1826* (2013.01)

(58) Field of Classification Search
None
See application file for complete search history.

(56) References Cited

U.S. PATENT DOCUMENTS

| | | | |
|---|---|---|---|
| 9,546,429 B1* | 1/2017 | Dion ................. | H01M 8/16 |
| 2005/0208343 A1* | 9/2005 | Kim ................. | H01M 4/92 |
| | | | 429/2 |
| 2010/0003543 A1* | 1/2010 | Zhou ................. | H01M 8/16 |
| | | | 429/2 |

OTHER PUBLICATIONS

Zhang et al. Submersible Microbial Fuel Cell Sensor for Monitoring Microbial Activity and BOD in Groundwater: Focusing on Impact of Anodic Biofilm on Sensor Applicability, 2011, Biotechnology and Bioengineering, vol. 108, No. 10, pp. 2339-2347 (Year: 2011).*
Cristiani et al. Cathodic and anodic biofilms in Single Chamber Microbial Fuel Cells, Biochemistry, Feb. 8, 2013, vol. 92, pp. 6-13 (Year: 2013).*
Lee et al. (Semi-continuous measurement of oxygen demand in wastewater using biofilm-capacitance, Bioresource Technology Reports, vol. 3, pp. 231-237, 2018) (Year: 2018).*

(Continued)

*Primary Examiner* — Neil N Turk
(74) *Attorney, Agent, or Firm* — Banner & Witcoff, Ltd.

(57) ABSTRACT

There is provided a biofilm capacitance microbial electrochemical cell (MEC) sensor to measure organic carbon in water and wastewater rapidly and accurately, represented by the 5-day biochemical oxygen demand ($BOD_5$). The MEC runs at charging (open circuit) and discharging (close circuit) conditions alternately to improve the sensitivity, response time and accuracy. The detectable $BOD_5$ concentrations with the biofilm-capacitance MEC range from 5 to 250 mg/L ($R^2>0.9$). The MEC sensor enables $BOD_5$ measurements at every 2 minutes (1 minute charging and 1 minute discharging), indicating semi-continuous quantification of organic carbon in water and wastewater.

8 Claims, 4 Drawing Sheets

(56) References Cited

OTHER PUBLICATIONS

Chang I.S., Jang J.K., Gil G.C., Kim M., Kim H.J., Cho B.W., Kim B.H. (2004) Continuous determination of biochemical oxygen demand using microbial fuel cell type biosensor. Biosensors and Bioelectronics 19, 607-613.

Dhar B.R., Ryu H, Ren H, Domingo J.W.S., Chae J., Lee, H.S. (2016) High biofilm conductivity maintained despite anode potential changes in a Geobacter-enriched biofilm. ChemSusChem 9, 3485-3491.

Dhar B.R., Elbeshbishy E., Hafez H., Lee H.S. (2015) Hydrogen production from sugar beet juice using an integrated biohydrogen process of dark fermentation and microbial electrolysis cell. Bioresource Technology 198, 223-230.

Government of Canada (2018) http://laws-lois.justice.gc.ca/eng/regulations/SOR-2012-139/FullText.html.

Kharkwal S., Tan Y.C., Lu M., Ng HY. (2017) Development and Long-Term Stability of a Novel Microbial Fuel Cell BOD Sensor with MnO2 Catalyst. Int J Mol Sci. 18, 276.

Kim B.H., Chang I.S., Gil G.C., Park H.S., Kim H.J. (2003) Novel BOD (biological oxygen demand) sensor using mediator-less microbial fuel cell. Biotechnology Letters 25, 541-545.

Sim J., An J., Elbeshbishy E., Ryu H., Lee H.S. (2015) Characterization and optimization of cathodic conditions for H2O2 synthesis in microbial electrochemical cells. Bioresource Technology 195, 31-36.

\* cited by examiner (A)

(B)

(C)

BIOCAPACITIVE BOD SENSOR

TECHNICAL FIELD

The present invention relates to a biocapacitive 5 day biochemical oxygen demand ($BOD_5$) sensor. In one aspect, $BOD_5$ is measured with the bio-capacitance of biofilm anodes.

BACKGROUND OF THE INVENTION

Preventing and monitoring water pollution from anthropogenic sources are significant for protecting nature and human health. Municipal wastewater is the largest water pollution source, which means that treatment and management of domestic wastewater is important. Organic compounds (called, carbonaceous organics or electron donors) are one of the important water quality parameters because they readily contaminate water and consequently can kill aquatic animals, deteriorating water environment. There are hundreds of organic compounds present in domestic wastewater, and hence it is almost impossible to quantify them individually. Instead of measuring individual organics (electron donors), electron acceptors have been quantified, given that electrons in the organics react with oxygen molecules in redox reactions. Hence, many scientists have called oxygen demand (OD) to represent organic content in water, which is a common parameter for assessing wastewater effluent quality. It is possible to measure OD chemically (chemical OD (COD)) or biochemically (biochemical OD (BOD)). Many municipalities have used the standard 5 day-BOD ($BOD_5$) that represents the amount of biodegradable organic compounds (or called carbonaceous organic compounds) present in wastewater. The change of electrons in the organics, the electron donors, is monitored with the change of dissolved oxygen, the electron acceptor, in biochemical redox reactions for 5 day-incubation. For instance, the Federal Government of Canada regulates $BOD_5$ concentration in wastewater effluent less than 25 mg/L.

The standard $BOD_5$ measurement method is time-consuming and labor-intensive due to long-term incubation for 5 days conducted by experts. In addition, $BOD_5$ measurement is intermittent (e.g. weekly or biweekly sampling and measurement) and thus cannot represent a continuously-varying $BOD_5$ concentration in wastewater effluent discharged into water bodies. In order to uninterruptedly ensure high quality wastewater effluent, a novel technology capable of monitoring $BOD_5$ in wastewater more frequently is essential.

Fluorescent or optical $BOD_5$ sensors have been developed, but their applicability is limited because of fundamental limitations: $BOD_5$ is the change of organic content by microbial redox reactions for 5 day-incubation, as described above. In this regard, microbial electrochemical cells (MECs) including microbial fuel cells (MFCs) are an attractive tool that could semi-continuously measure $BOD_5$ concentration in water, since anode-respiring bacteria (ARB) can transfer electrons mainly from biodegradable organic matter to the anode in MECs. Previous studies have developed $BOD_5$ monitoring tools based on the MEC's fundamental, and have used electric current (or voltage) as a signal to surrogate $BOD_5$ concentrations in wastewater; see for example Chang I. S, et al, *Continuous determination of biochemical oxygen demand using microbial fuel cell type biosensor*, Biosensors and Bioelectronics 19, 607-613, 2004; Kim B. H. et al, *Novel BOD (biological oxygen demand) sensor using mediator-less microbial fuel cell*, Biotechnology Letters 25, 541-545, 2003; and Kharkwal S. et al, *Development and Long-Term Stability of a Novel Microbial Fuel Cell BOD Sensor with $MnO_2$ Catalyst*, Int J Mol Sci. 18, 276, 2017. However, electric current is an inherently kinetic term that measures the oxidation rate of organic compounds by ARB. Surrogating $BOD_5$ concentration with electric current (kinetics term, 1 A=1 C/s) could work for certain conditions, but in principle using the kinetic term for $BOD_5$, concentration term or mass term in fixed volume, does not make sense. Moreover, electric current (or current density) or voltage generated from MECs does not well represent low $BOD_5$ concentration and its small change (Kharkwal et al.).

There are no solutions to address the sensitivity limitation of MFC- and MEC-based $BOD_5$ sensors. A solution is required to improve MEC-based $BOD_5$ sensors.

SUMMARY

Cumulative coulombs in a given time (coulombs=current×time) are equivalent to substrate electrons oxidized anaerobically by ARB, and hence the mass term of cumulative coulombs can better represent $BOD_5$ concentration in a fixed volume. Cumulative coulombs can also have high sensitivity to low $BOD_5$. Typical continuous operation of MECs in close-circuit mode may produce cumulative coulombs to steady $BOD_5$ concentration. However, it is challenging to measure changing $BOD_5$ concentration with close-circuit MECs because ARB's metabolism and current generation do not sensitively respond to a change of $BOD_5$ concentration in continuous mode; it is difficult to differentiate cumulative coulombs to $BOD_5$ between wastewater samples in continuous mode.

In the present invention the bio-capacitance of biofilm anodes generated under open and close circuit operation are used to provide accurate measurement of $BOD_5$ in a semi-continuous manner. ARB keeps oxidizing and transferring donor electrons to biofilm anodes in MECs run in an open circuit, and a high discharging current is generated right after close-circuit operation, suggesting bio-capacitance of biofilm anodes. In one aspect of the present invention, the bio-capacitance in biofilm anodes under open circuit (charging substrate's electrons) and close circuit (discharging the electrons) allows production of cumulative coulombs in response to given $BOD_5$ concentration. High discharging current in close circuit mode right after open circuit well represents donor electrons transferred to the biofilm anodes, and this discharging current can separate cumulative coulombs to $BOD_5$ between wastewater samples. In the present invention biofilm anodes act as a bio-capacitor quantitatively well surrogated organic concentration, measuring a low $BOD_5$ concentration in wastewater.

In one aspect of the present invention, $BOD_5$ is measured with bio-capacitance of biofilm anodes. Electrons are transferred to biofilm anodes catalyzed by ARB in open-circuit mode and the electrons in closed-circuit mode are monitored as cumulative coulombs.

In one embodiment, the present invention is able to measure (1) a low $BOD_5$ concentration below 5 mg/L, (2) a small change of $BOD_5$ in continuously changing environment, and (3) semi-continuous manners, once per 6 minutes.

In this manner, the present invention addresses the most critical challenge of MEC-based $BOD_5$ sensors, namely, the sensitivity issue.

In one aspect of the present invention there is provided a biocapacitive BOD sensor comprising: a microbial electrochemical cell (MEC) having a biofilm anode and a biofilm cathode, the biofilm anode working as a capacitor; and a reference electrode optionally inserted into the cell to fix the anode potential; wherein the MEC is run at charging (open circuit) and discharging (close circuit) conditions alternately; and wherein bio-capacitance of the biofilm anode indicates organic carbon concentration.

In a further aspect of the present invention the biocapacitive BOD sensor is used for sensing other organic compounds including organic carbon, non-biodegradable compounds, or toxics.

In a further aspect of the present invention the biocapacitive BOD sensor is used by power suppliers to measure the organic carbon concentration in water.

In a further aspect of the present invention the biocapacitive BOD sensor comprises more than one MEC stacked in serial or parallel to power the BOD sensor.

In a further aspect of the present invention, there is provided a system comprising the biocapacitive BOD sensor integrated with one or more other devices to improve biodegradability or reliability between cumulative coulombs and oxygen demand.

In a further aspect of the present invention there is provided a BOD sensor wherein the biofilm anode has ARB as the dominant microorganism.

In yet a further aspect of the present invention the BOD sensor further comprises a separator partitioning the anode and the cathode.

In yet a further aspect of the present invention, there is provided a BOD sensor wherein electrons are transferred to biofilm anodes catalyzed by ARB in open-circuit mode and the electrons in closed-circuit mode are monitored as cumulative coulombs.

BRIEF DESCRIPTION OF THE DRAWINGS

The invention will be better understood with reference to the following drawings showing exemplary embodiments in which.

DESCRIPTION OF THE PREFERRED EMBODIMENTS

Figure 1:
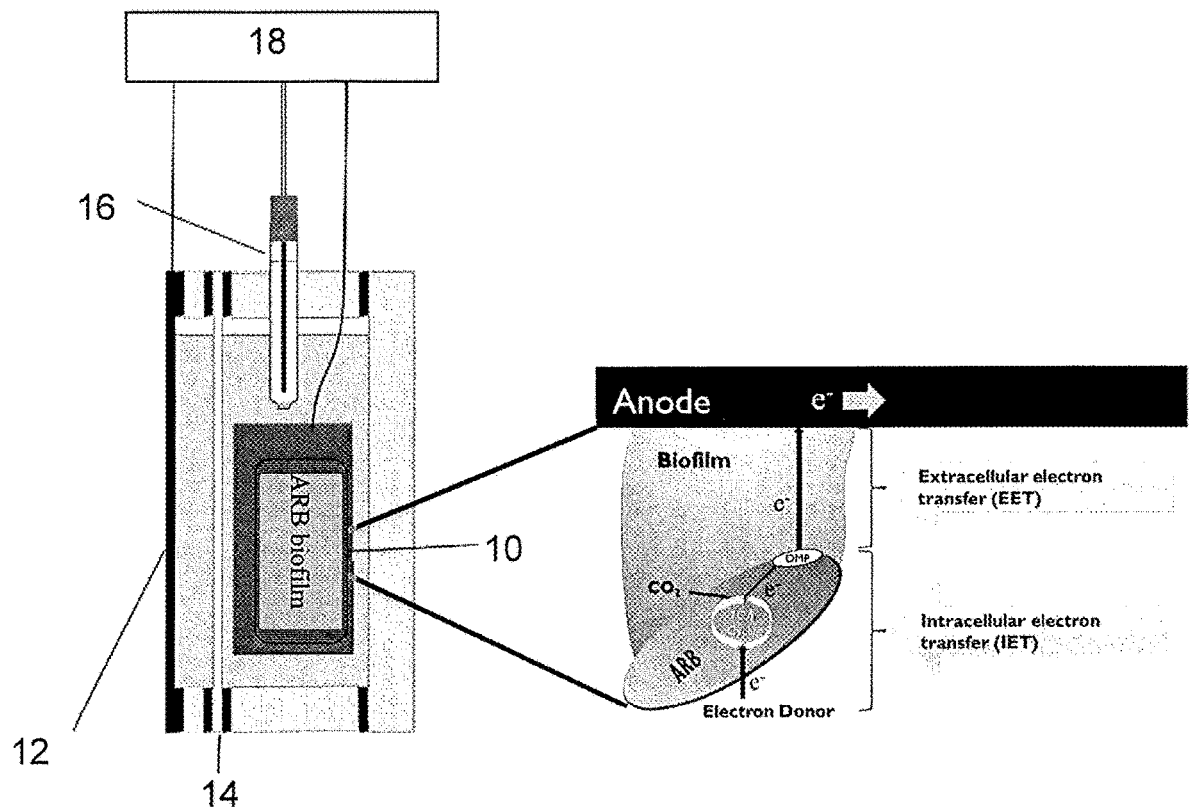
FIG. 1 shows a schematic of a microbial electrochemical cell employed in an exemplary experiment.

In one exemplary embodiment of the present invention, there is provided a laboratory-scale MEC, as shown in FIG. 1. It consists of cylindrical acrylic sections and has a working volume of 19.20 mL and 4.80 mL for the anode and the cathode chamber, respectively. In this embodiment, carbon felt 10 (for example, 43201, Alfa Aesar, USA) with a geometric surface area of 16 cm² was selected as the anode while an air cathode consisting of carbon cloth 12 with a platinum/carbon black catalyst layer (for example, 0.5 mg Pt/cm²; SLGDE, Fuel Cells Etc, USA) is the cathode. ARB biofilm is formed on the surface of the anode. An electron donor (typically organic compound expressed with BOD concentration) is transported to ARB. The electron donor is oxidized via anaerobic citric acid cycle, and the electrons released from anaerobic citric acid cycle is transferred to outer membrane proteins (OMP); the electron transfer from the electron donor to OMP is called intracellular electron transfer (IET). Then, the electrons in OMP is transported to the anode throughout the biofilm, and this reaction occurs outside of ARB cells, called extracellular electron transfer (EET). The anode and the cathode chamber are partitioned by a cation exchange membrane 14 (for example, CEM; CM1 7000, Membranes International, USA) with a projected surface area of 8.04 cm², while other types of separators can work. An Ag/AgCl reference electrode 16 (for example, MF 2052, BASI, USA) is inserted ~0.5 cm away from the anode 10 to fix the anode potential ($E_{anode}$) at −0.4 V (vs Ag/AgCl) using a potentiostat 18 (e.g. VSP, BioLogic, France).

In this exemplary embodiment, the MEC was inoculated with 5 mL of effluent from an existing MEC that had been operated with acetate medium (25 mM acetate medium) for over 1 year. The composition of the medium was (per L of 18.2 MΩ cm MilliQ water) 2050 mg/L $CH_3COONa$, 2274 mg $KH_2PO_4$, 11,678 mg $Na_2HPO_4 \cdot 12H_2O$, 37 mg $NH_4Cl$, 25 mg $MgCl_2 \cdot 6H_2O$, 6 mg $MnCl_2 \cdot 4H_2O$, 0.1 mg $CuSO_4 \cdot 5H_2O$, 0.1 mg $Na_2WO_4 \cdot 2H_2O$, 0.1 mg $NaHSeO_3$, 0.01 mg $CaCl_2 \cdot 2H_2O$, 0.5 mg $ZnCl_2$, 0.1 mg $AlK(SO_4)_2$, 0.1 mg $H_3BO_3$, 0.1 mg $Na_2MoO_4 \cdot 2H_2O$, 0.2 mg $NiCl_2$, 5 mg EDTA, 1 mg $CO(NO_3)_2 \cdot 6H_2O$, and 0.2 mg $NiCl_2 \cdot 6H_2O$. The medium was autoclaved and sparged with ultra-pure nitrogen (99.999%) for 30 min. Then, $FeCl_2 \cdot 2H_2O$ (20 mM) and $Na_2S \cdot 9H_2O$ (77 mM) were added to the medium (1 mL per L). Medium pH was constant at 7.3±0.1. The cathode chamber was filled with tap water in which oxygen reduction to water occurred (see further details in Dhar B. R. et al, *High biofilm conductivity maintained despite anode potential changes in a Geobacter-enriched biofilm*, ChemSusChem 9, 3485-3491, 2016 and Sim J. et al, *Characterization and optimization of cathodic conditions for $H_2O_2$ synthesis in microbial electrochemical cells*, Bioresource Technology 195, 31-36, 2015).

In this embodiment, during ARB acclimation, the anode and the cathode chamber are operated in semi batch mode until a consistent peak current density (~0.98 A/m²) is repeatedly obtained. Then, the MEC is switched from semi batch to continuous mode by feeding acetate medium to the anode chamber using a peristaltic pump (Masterflex 7523-80, Cole-Parmer, USA) at a hydraulic residence time (HRT) of 8 h and operating in continuous mode until a steady state current density was achieved for each acetate concentration. During biocapacitance tests, the operation of the MEC was alternated between the open circuit mode (electron charging) and closed circuit mode (electron discharging) with the EC-Lab software included with the potentiostat 18. During open circuit mode, the biofilm oxidizes electron donor (e.g., acetate) and stores the metabolized electrons in the biofilm anode (bio-capacitance). During closed circuit mode, the anode and cathode are connected, and the stored electrons are discharged to the cathode. Two charging times of 15 min and 30 min (open circuit mode) were assessed with fixed discharging time of 1 min (closed circuit mode). Five cycles of open and closed circuit modes were tested as acetate concentration was varied from 32 to 258 mg COD/L.

Calibration curves were established between the cumulative coulombs in a 1 min-discharging time and acetate concentration (as mg COD/L).

After completing proof-of-concept experiments with acetate medium, testing was performed using the MEC as an OD sensor with domestic wastewater. The effluents from primary and secondary clarifiers were regularly sampled from a Waterloo wastewater treatment plant in Ontario, Canada. The effluents were diluted with deionized water to create different BOD concentrations and calibration curves were built against cumulative coulombs. Current and electrode potentials were monitored 100 times every second using the potentiostat with EC-Lab.

In one aspect of the present invention, a key innovation is to use biofilm capacitance in MECs to measure $BOD_5$ concentration or in general organic carbon by operating MECs at open and close circuit modes alternately. MECs are fuel cells employing microorganisms as an electrode catalyst (typically anode, but can be applied for cathode). The MECs in one aspect consist of microorganisms, electrodes (e.g., anodes and cathodes), separators, and external wires. The MECs can be operated as two electrodes (fuel cell mode) or more than two electrodes including reference electrodes (e.g., three or four electrodes).

In one embodiment, microorganisms, such as ARB (or called, exoelectrogens), are used for the electrode catalyst, but any biotic and abiotic substances (e.g., enzymes, metals, etc.) can be applied to the capacitance-based BOD sensor integrated with alternative operation of systems between open and close circuit.

Any conductive and semi-conductive materials can be used as electrodes, regardless of size, which means nano- and micro-sized materials (e.g. carbon nanomaterials) can be applied to the capacitive BOD sensor.

Ion exchange membranes are typically used as the separator between the anode and cathode to stop short circuit in systems. However, any non-conductive materials can be used as the separator. Alternatively, in one aspect of the present invention the capacitive BOD sensor does not employ a separator, and is thus a single-chamber MEC. Any conductive materials can be used for external wires (e.g., copper, titanium, etc.).

Any materials that can provide physical rigidity to microorganisms, electrodes, and systems can be used for MEC bodies, which include plastics, papers, glasses, metals, organic and inorganic composites, etc.

In one embodiment of the present invention there is included an alternate operation between open and close circuit for cumulating substrate electrons in biofilms on the electrodes. 1 minute and 5 minutes are suggested as the optimum charging time, followed by a 1 minute discharging time. However, shorter or longer charging and discharging time for cumulating substrate electrons in the biofilms can be applied to the capacitance BOD sensor. Water samples can be introduced to the sensor continuously and discontinuously. External power suppliers, potentiostats, or any devices that help accumulate substrate electrons in the biofilms or improve the stability of biofilm catalytic functions can be applied to this invention; here external power suppliers mean any kinds of energy externally given to the sensor, including sunlight, wind, wave, thermal, geothermal, biomass, and so on. For instance, photovoltaics can be used as the external power supplier to the sensor.

The cylinder shape of MECs is preferred for design and manufacture, but any shape of MECs can be applied if the capacitance is utilized for measuring organic carbon concentration. In one embodiment, a dual-chamber MEC is used, however, single and multiple chambers can be applied for the capacitance BOD sensor.

The biofilm capacitance BOD sensor can be installed at a fixed location as a stationary sensor. Alternatively, the capacitive sensor can be placed in a mobile environment. For instance, dozens of the capacitance BOD sensors can be floated in the middle of Lake Ontario by combining the sensors with buoys.

In one application the capacitance BOD sensor can be used as "an alarming device" in wastewater treatment facilities or sensitive water bodies (e.g., water resources). For instance, municipal wastewater treatment facilities (e.g., city of Toronto or Chicago) continuously receive domestic wastewater from houses and buildings and keep treating the wastewater. This means that treated wastewater is continuously discharged to water bodies, but the current monitoring regulations only require weekly, biweekly or monthly measurements of $BOD_5$ concentration in the effluent. These monitoring practices cannot guarantee that the $BOD_5$ concentrations regularly measured weekly, biweekly or monthly cannot represent the quality of wastewater effluent continuously discharged: The current monitoring practices are statistically very poor. Simply increasing the frequency of $BOD_5$ measurements with the standard 5-day method might improve the statistical quality of $BOD_5$ concentration, but this option needs high investment and maintenance costs. In comparison, the biofilm capacitance sensor of the present invention can signal $BOD_5$ concentration in water at every 2-6 min, which means that it can measure $BOD_5$ concentration 1,680-5,040 times per week, instead of a single measurement per week in the current monitoring regulation. This substantial increase of frequency of $BOD_5$ data will improve the quality of statistical $BOD_5$ concentration, ensuring clean wastewater effluent or requirement of post-treating the effluent. For example, when the biofilm capacitance sensor signals $BOD_5$ concentration over 25 mg/L (the maximum allowable $BOD_5$ concentration in wastewater effluent), lab technicians or operators can immediately sample treated wastewater and measure $BOD_5$ concentration according to the 5-day standard $BOD_5$ method; then, one can ensure a high quality of wastewater effluent or add a tertiary post-treatment process. They can simply keep following the current monitoring regulation when the sensor does not give the alarming signal (<25 mg/L). For these reasons, the biofilm capacitance BOD sensor can address the critical limitation of the current monitoring practices by installing the sensor on-site in domestic wastewater treatment facilities.

In a further aspect, the present invention can be used to apply the biofilm capacitance sensor to organic carbon in lakes, rivers or groundwater to monitor the quality of water, mostly water resources. The principle of measuring organic carbon is similar to that of $BOD_5$ in water and wastewater.

Figure 2:
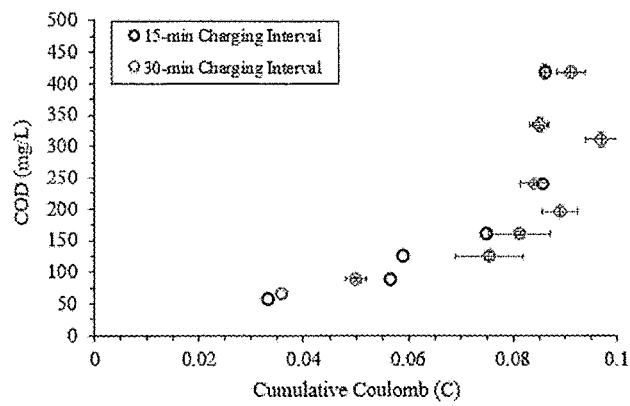
FIG. 2 shows the relationship between acetate concentration (in COD mg/L) and cumulative coulombs for 15-min and 30-min charging interval. (A) shows a Monod pattern curve, (B) shows a linear correlation below 250 mg COD/L with 15 min-charging time, and (C) shows a linear correlation below 200 mg COD/L with 30 min-charging time. The discharging time was fixed at 1 min.
Figure 2:
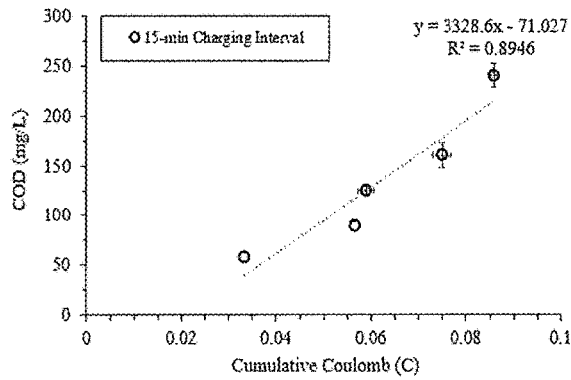
Figure 2:
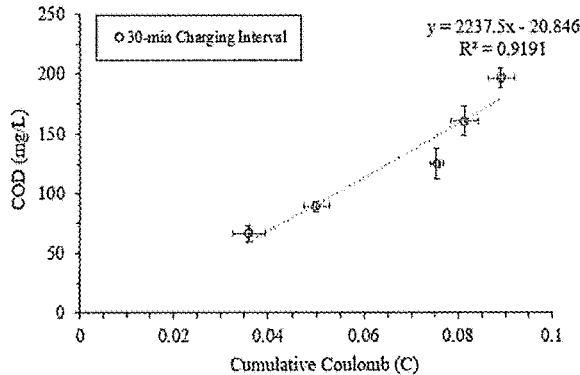
Figure 3:
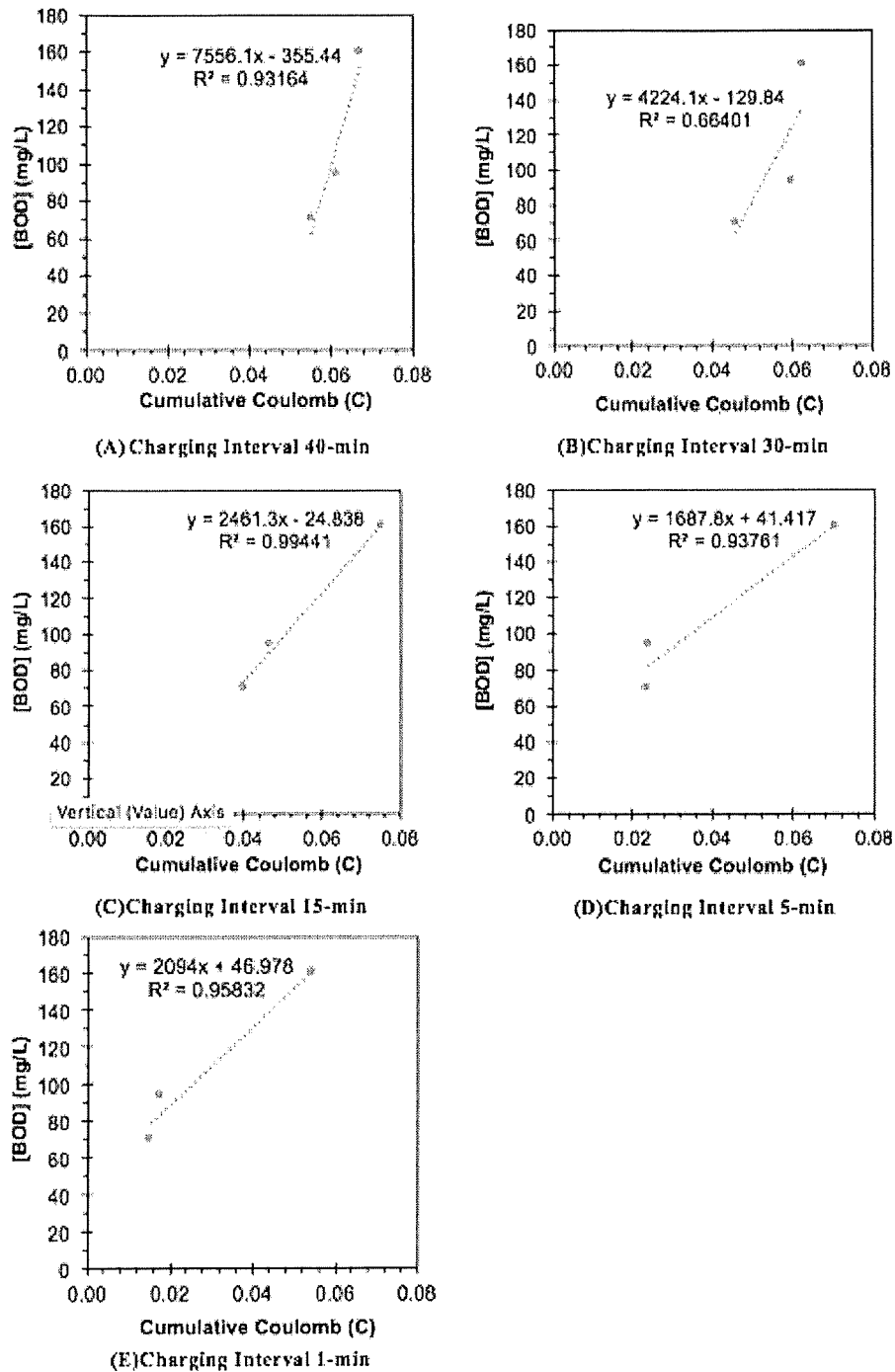
FIG. 3 shows the linearity between domestic wastewater and cumulative coulombs built in the MEC. Charging time was varied between 1 and 40 min, and discharging time was fixed at 1 min for the experiments. $BOD_5$ measurements were conducted in duplicate.
Figure 4:
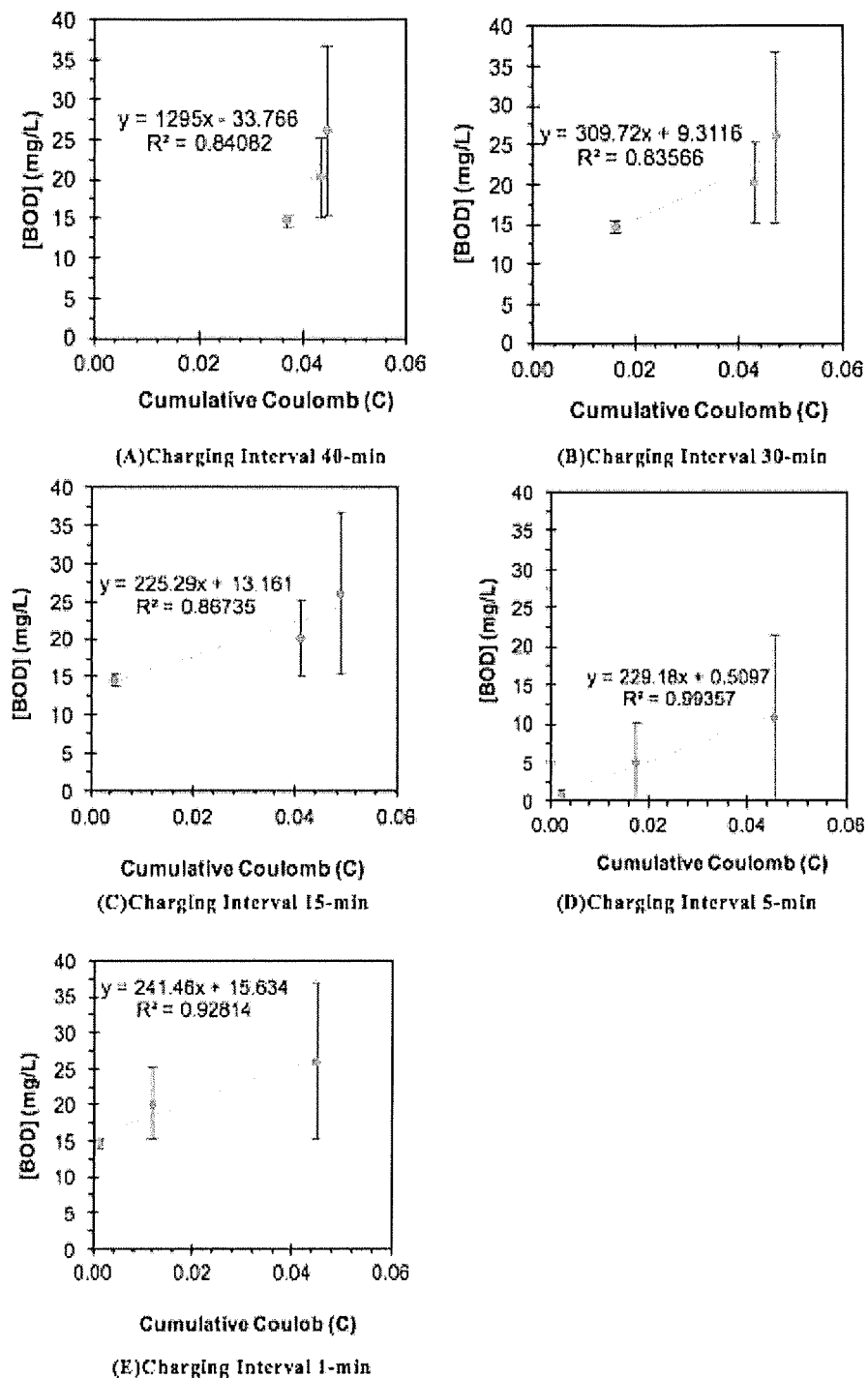
FIG. 4 shows the linearity between wastewater effluent and cumulative coulombs in the MEC. Discharging time was fixed at 1 min during the experiments.

Testing results are shown in FIGS. 2 to 4.

Cumulative coulombs in discharging mode and acetate concentration were plotted at FIG. 2. Cumulative coulombs were linearly increased to acetate concentration at ~200 mg COD/L, but the coulombs were saturated at over acetate concentration of ~200 mg/L (1 mM acetate=64 mg COD/L). This pattern is almost same to current density and substrate (j-S) curves.

Equation 1 below describes the Monod equation that correlates substrate-utilization rate with substrate concentration.

$$(-dS_d/dt) = f_e^o q_{max,app} \frac{S_d}{S_d + K_{sd,app}} X_a \quad (1)$$

where, $S_d$ is donor substrate concentration (g COD/L), t is reaction time (d), $f_e^o$ is the fraction of electrons used for catabolism, $q_{max}$ is the apparent maximum specific substrate utilization rate (g COD/g VS-d), $K_{sd,app}$ is the apparent half-saturation concentration of substrate (g COD/m$^3$), and $X_a$ is the concentration of active microorganisms (g VS/m$^3$).

For biofilm anodes, (−dS/dt) per anode area is equivalent to current density (1 g COD/d-m$^2$=0.14 A/m$^2$), and current density is mathematically described as below.

$$j = 0.14 f_e^o q_{max,app} X_f L_f \frac{S_d}{S_d + K_{sd,app}} \quad (2)$$

where, j is current density per geometric surface area of the anode (A/m$^2$), 0.14 is the conversion factor (0.14 A=1 g COD/d), $X_f$ is biofilm density (g VS/m$^3$), and $L_f$ is biofilm thickness (m).

Cumulative coulombs, that are the products of j×t in a given time, can represent current density, so the correlation between the coulombs and acetate can show Monod-like curves, as shown in FIG. 2(A). In addition, the Monod-like curve obtained from charging and discharging operation supports that ARB keeps oxidizing acetate, transfers acetate electrons to the biofilm, and stores the electrons in the biofilm, i.e. bio-capacitor. FIGS. 2(B) and 2(C) show that a linear correlation (R$^2$~0.9) was obtained between cumulative coulombs and acetate concentration <250 mg COD/L. The linear curves suggest that cumulative coulombs established in charging and discharging operation of the MEC can surrogate acetate concentration less than 250 mg COD/L. This indicates that MECs can be used for measuring COD or BOD concentration in semi-continuous manners once every 16 minute (15 minute charging and 1 minute discharging).

Correlation tests were extended (cumulative coulombs versus BOD$_5$) with domestic wastewater and wastewater effluent from activated sludge; the process as charging time (open circuit) was changed from 1 min to 40 min. FIG. 3 shows the high linearity between wastewater BOD$_5$ and cumulative coulombs for domestic wastewater (R$^2$ 0.93-0.99), except for 30 min charging. Interestingly, 1 min-charging condition still showed high linearity (R$^2$=0.96), which means that the present invention is able to measure OD concentration at every 2 minute (1 minute charging and 1 minute discharging).

The BOD$_5$ concentration in the wastewater effluent was further correlated with cumulative coulombs in FIG. 4. BOD$_5$ concentration was deviated in triplicate measurements probably due to sampling bias (e.g., suspended solids). R$^2$ regression coefficient between cumulative coulombs and BOD$_5$ tended to decrease in the wastewater effluent <~25 mg BOD$_5$/L, as compared to influent domestic wastewater. However, the 5 min-charging presented the high linearity of R$^2$=0.99, indicating BOD$_5$ measurement once every 6 minute (5 minute charging and 1 minute discharging).

It will be appreciated by one skilled in the art that variants can exist in the above-described arrangements and applications. The scope of the claims should not be limited by the preferred embodiments set forth in the examples, but should be given the broadest interpretation consistent with the description as a whole. For example, a system can integrate the biocapacitive BOD sensor with other devices (e.g., chemical oxidation, physical filtration, etc.) to improve biodegradability or reliability between cumulative coulombs and oxygen demand.

The invention claimed is:

1. A system for monitoring a biochemical oxygen demand (BOD) or an organic carbon concentration comprising:
   a biocapacitive sensor comprising:
      a microbial electrochemical cell (MEC) having a biofilm anode and a cathode, wherein the MEC is configured to continuously alternate between operation modes comprising a charging, open circuit mode and a discharging, closed circuit mode;
   a processing circuitry coupled to the biocapacitive sensor, wherein the processing circuitry is configured to:
      determine an operation mode associated with the MEC;
      measure a production of cumulative coulombs in the MEC during the discharging, closed circuit mode following the charging, open circuit mode; and
      determine the biochemical oxygen demand or the organic carbon concentration from the measured production of the cumulative coulombs.

2. The system of claim 1, further comprising an external power supply.

3. The system of claim 1, further comprising more than one MEC stacked in serial or parallel.

4. The system of claim 1, wherein the biofilm anode has anode-respiring bacteria (ARB) as a dominant microorganism.

5. The system of claim 1, further comprising a separator partitioning the biofilm anode and the cathode.

6. The system of claim 1, wherein the measured production of the cumulative coulombs are equivalent to substrate electrons oxidized anaerobically by ARB.

7. The system of claim 1, further comprising a reference electrode inserted into the MEC to fix a potential of the biofilm anode.

8. The system of claim 1, wherein the MEC comprises a plurality of chambers.

* * * * *